United States Patent [19]

Cooperman et al.

[11] Patent Number: 5,674,708
[45] Date of Patent: Oct. 7, 1997

[54] α-1-ANTICHYMOTRYPSIN ANALOGUES HAVING ELASTASE INHIBITORY ACTIVITY

[75] Inventors: Barry S. Cooperman, Penn Valley; Harvey Rubin, Philadelphia; Norman Schechter, Philadelphia; Zhi Mei Wang, Philadelphia, all of Pa.

[73] Assignee: Trustees of the University of Pennsylvania, Philadelphia, Pa.

[21] Appl. No.: 221,078

[22] Filed: Mar. 31, 1994

Related U.S. Application Data

[63] Continuation-in-part of Ser. No. 5,898, Jan. 15, 1993, abandoned, and Ser. No. 5,908, Jan. 15, 1993, Pat. No. 5,367,064, each is a division of Ser. No.735,322, Jul. 24, 1991, Pat. No. 5,266,465, which is a division of Ser. No. 370,704, Jun. 23, 1989, Pat. No. 5,079,336.

[51] Int. Cl.$^6$ .............. C12N 15/15; C12N 1/21; A61K 38/55; C07K 14/81
[52] U.S. Cl. .............. 435/69.2; 435/172.3; 435/240.2; 435/252.3; 514/2; 514/12; 530/350; 536/23.1; 536/23.5
[58] Field of Search .............. 435/69.2, 172.3, 435/240.2, 252.3; 514/2, 12; 530/350; 536/23.1, 23.5

[56] References Cited

U.S. PATENT DOCUMENTS

| | | | |
|---|---|---|---|
| 4,732,973 | 3/1988 | Barr et al. | 530/350 |
| 4,916,117 | 4/1990 | Lezdey et al. | 514/8 |
| 5,008,242 | 4/1991 | Lezdey et al. | 514/8 |
| 5,079,336 | 1/1992 | Rubin et al. | 530/350 |
| 5,252,725 | 10/1993 | Rubin et al. | 536/23.5 |
| 5,266,465 | 11/1993 | Rubin et al. | 435/69.2 |

OTHER PUBLICATIONS

Ardelt and Laskowski, Turkey Ovomucoid Third Domain Inhibits Eight Different Serine Prtoeinases of Varied Specificity on the Same . . . Leu$^{18}$–Glu$^{19}$ . . . Reactive Site *Biochemistry*, 1985, 24, 5313.

Bainton, et al., Differences in Enzyme content of Azurophil and Specific Granules of Polymorphonuclear Leukocytes *J. Cell Biol,* 1968, 39, 286.

Bainton, et al., Differences in Enzyme Content of Axurophil and Specific Grnaules of Polymorphonulcear Leukocytes *J. Cell Biol.,* 1968, 39, 299.

Cooperman et al. Antichymotrypsin Interaction with Chymotrypsin *J. Biol. Chem.* 1993 268:23616–23625.

Baird et al., *J. Appl. Physiol.,* 1986, 61, 2224.

Beatty et al. Kinetics of Association of Serine Proteinases with Native and Oxidized α-1-Proteinase Inhibitor and α-1-Antichymotrypsin *J. Biol. Chem.* 1980.

Campbell, et al., Proteolysis by Neutrophils; Relative importance of cell–substrate contact and oxidative inactivation of proteinase inhibitors in vitro *J. Clin. Invest.,* 1982, 70, 845.

Camussi, G. et al., Synthesis and Release of Platelet–Activating Factor is Inhibited by Plasma α1–Proteinase Inhibitor or α1–Antichymotrypsin and is stimulated by Proteinases *J. Exp. Med.,* 1988, 168, 1293.

Carrell et al. Plakalbumin, α$_1$–antitrypsin, antithrombin and the mechanism of inflammatory thrombosis *Nature* 1985 317:730–732.

Camussi, G. et al., Tumor Necrosis Factor Stimulates human neutrophils to release leukotriene B$_4$ and platelet–activating factor *Eur. J. Biochem.,* 1989, 182, 661.

Chandra et al. Sequence Homology between Human α1–Antichymotrypsin, α1–Antitrypsin, and Antithrombin III *Biochemistry* 1983 22:5055–5060.

Petersen and Clemmensen, Kinetics of Plasmin Inhibition in the Presence of a Synthetic Tripeptide substrate *Biochem. J.,* 1981, 199, 121.

Redens et al., Synergistic Protection from Lung Damage by Combining Antithrombin–III and Alpha1–Proteinase Inhibitor in the *E. coli* Endotoxemic Sheep Pulmonary Dysfunction Model *Circ. Shock,* 1988, 26, 15.

Rosengren et al., Neutrophil–mediated vascular leakage is not suppressed by leukocyte elastase inhibitors *Am. J. Physiol.,* 1990, 259, H1288.

Potempa, et al., Proteolytic Inactivation of α–1–Antichymotrypsin sites of cleavage and generation of chemotactic activity *J. Biol. Chem.,* 1991, 266, 21482.

DelMar et al., A Sensitive New Substrate for Chymotrypsin *Anal. Biochem.* 1979, 99, 316.

Emerson et al., Protection Against Disseminated Intravascular Coagulation and Death by Antithrombin–III in the *Escherichis coli* Endotexemic Rat *Circ. Shock,* 1987, 21, 1.

Hill et al. Plasma Protease Inhibitors in mouse and man *Nature* 1984 311:175–177.

Nagai et al., Administration of α$_1$–Proteinase Inhibitor Ameliorates Bleomycin–induced Pulmonary Fibrosis in Hamsters *Am. Rev. Resp. Dis.,* 1992, 145, 651.

Kilpatrick et al., Inhibition of Human Neutrophil Superoxide Generation by ®1–Antichymotrypsin *J. Immunol.,* 1991, 146, 2388.

Laemmli, U.K. Cleavage of Structural Proteins during the Assembly of the Head of Bacteriophage T4 *Nature (London)* 1970 227:680–685.

Maniatis et al. Molecular Cloning: A Laboratory Manual, Cold Spring Harbor Laboratory Press, Cold Spring Harbor, New York, 1982 249–255.

Morii et al. Amino Acid Sequence at the Reactive Site of Human α$_1$–Antichymotrypsin *J. Biol. Chem.* 1983 258:12749–12752.

Nathan, Neutrophil Activation on Biological Surfaces *J. Clin. Invest.,* 1980, 80, 1550.

(List continued on next page.)

*Primary Examiner*—Vasu S. Jagannathan
*Assistant Examiner*—David S. Romeo
*Attorney, Agent, or Firm*—Law Offices of Jane Massey Licata

[57] ABSTRACT

The present invention provides an analogue of human α-1-antichymotrypsin wherein the amino acid at position 358 is selected from the group consisting of isoleucine, valine, alanine, aspattic acid, threonine, and glutamic acid.

34 Claims, 5 Drawing Sheets

OTHER PUBLICATIONS

Renesto, P. et al., Tumor Necrosis Factor–α Enhances Platelet Activation Via Cathepsin G Released From Neutrophils *J. Immunol.*, 1991, 146, 2305.

Sambrook et al., *Molecular Cloning: A Laboratory Manual*, second edition, Cold Spring Harbor Laboratory Press, Cold Spring Harbor, NY (1989).

Sanger et al., DNA sequencing with chain–terminating inhibitors *Proc. Nat'l. Acad. Sci, U.S.A.*, 1977, 74, 5463.

Schechter et al. Reaction of Human Chymase With Reactive Site Variants of α1–Antichymotrypsin *J. Biol. Chem.* 1993 268:23626–23633.

Schonbaum et al., The Spectrophotometric Determination of the Operational Normality of an α–Chymotrypsin Solution *J. Biol. Chem.*, 1961, 236, 2930.

Studier and Moffatt, Use of Bacteriophage T7 RNA Polymerase to Direct Selective High–leve Expression of Cloned Genes *J. Mol. Biol.*, 1986, 189, 113.

Towbin et al. Electrophoretic transfer of proteins from polyacrylamide gels to nitrocellulose sheets *Proc. Nat'l Acad. Sci. USA* 1979 76:4350–4354.

Travis and Fritz, Potential Problems in Designing Elastase Inhibitors for Therapy *Am. Rev. Resp. Dis.* 1991, 43, 1412.

Tsuda et al.,Purification, Properties and Identification of A Serum DNA Binding Protein and Its Microheterogeneity *J. Exp. Clin. Med.*, 1982, 7, 201.

Wachter et al. Cloning A Serine Protease Inhibitor Gene With An Antibody Specific Probe Abstract, Jan. 1987, American Academy of Allergy and Immunology.

Wachter et al. Cloning an Antigenic Determinants of Serine Protease Inhibitors Abstract, Jan. 1987, 43 Annual Meeting, Annals of Allergy.

Weiss, et al., Neutrophil–Mediated Solubilzation of the Subendothelial Matrix: Oxidative and nonoxidative mechanisms of proteolysis used by normal and chronic granulomatous disease phagcytes *J. Immunol.*, 1986, 136, 636.

Young and Davis, Efficient isolation of genes by using antibody probes *Proc. Natl. Acad. Sci., U.S.A.*, 1977, 74, 5463.

Young et al. Efficiient isolation of genes by using antibody probes *Proc. Natl. Acad. Sci. USA* 1983 80:1194–1198.

Rubin et al. Cloning, Expression, Purification, and Biological Activity of Recombinant Native and Variant Human α1–Antichymotrypsins *J. Biol. Chem.* 1990 265:1199–1207.

Rubin, H. The Design and Development of Protease Inhibitors as Therapeutic Agents BOOK CITATION Ch.28 pp. 183–196.

Jallat et al. Prot. Eng. 1986 1:29–35.

Abstract Phagocyte Workshop Washington, DC Apr. 28, 1989.

Kilpatrick et al. Native and Recombinant α–1 Antichymotrypsin (ACT) Inhibit Superoxide Anion ($O_2-$) Generation in Human Neutrophils Society for Leukocyte Biology Marco Island, Fl 1989.

Schoenberger et al. Limited proteolysis of C1–inhibitor by chymotrypsin–like proteinases *FEBS Letters* 1989 259:165–167.

Schechter et al. On The Size of The Active Site In Proteases *Biochem. and Biophy. Res. Comm.* 1967 27:157–162.

Nakajima et al. Mapping the Extended Substrate Binding Site of Cathepsin G and Human Leukocyte Elastase *J. Biol. Chem.* 1979 254:4027–4032.

Meister et al. Immunohistochemical Characterization of Hitiocytic Tumours *Diagnostic Histopathology* 1981 4:79–87.

Rubin H. The Biology and Biochemistry of Antichymotrypsin and its Potential Role as a Therapeutic Agent *Biol Chem* 1992 373:497.

Wei et al. Crystallization, Activity Assay and preliminary X–ray Diffraction Analysis of the Uncleaved Form of the Serpin Antichymotrypsin *J. Mol. Biol.* 1992 226:273–276.

```
          10           20            30             40            50
          |            |             |              |             |
[CTC TGC CAC CCT] AAC AGC CCA CTT GAC GAG GAG AAT CTG ACC CAG GAG AAC CAA
 Leu Cys His Pro  Asn Ser Pro Leu Asp Glu Glu Asn Leu Thr Gln Glu Asn Gln 60            70            80            90           100
              |             |             |             |             |
GAC CGA GGG ACA CAC GTG GAC CTC AAG CAG TTA GCC TCC AAC GTG GAC TTC GCT
Asp Arg Gly Thr His Val Asp Leu Lys Gln Leu Ala Ser Asn Val Asp Phe Ala 110           120           130           140           150           160
|             |             |             |             |             |
TTC AGC CTG TAC AAG CAG TTA GTC CTG CTG AAG GCC CCT GAT AAG AAT GTC ATC TTC
Phe Ser Leu Tyr Lys Gln Leu Val Leu Leu Lys Ala Pro Asp Lys Asn Val Ile Phe 170           180           190           200           210
          |             |             |             |             |
TCC CCA CTG AGC ATC TCC ACC GCC TTG GCC TTC CTG TCT CTG GGG GCC CAT AAT
Ser Pro Leu Ser Ile Ser Thr Ala Leu Ala Phe Leu Ser Leu Gly Ala His Asn 220           230           240           250           260           270
|             |             |             |             |             |
ACC ACC CTG ACA GAG ATT CTC AAA GGC CTG CTG AAG TTC AAC CTC ACG GAG ACT TCT
Thr Thr Leu Thr Glu Ile Leu Lys Gly Leu Leu Lys Phe Asn Leu Thr Glu Thr Ser 280           290           300           310           320
          |             |             |             |             |
GAG GCA GAA ATT CAC CAG AGC TTC CAG CAC CTC CGC ACC CTC AAT CAG TCC
Glu Ala Glu Ile His Gln Ser Phe Gln His Leu Arg Thr Leu Asn Gln Ser
```

Fig. 1a

```
330
AGC GAT GAG CTG CAG CTG AGT ATG GGA AAT GCC ATG TTT GTC AAA GAG CAA CTC
Ser Asp Glu Leu Gln Leu Ser MET Gly Asn Ala MET Phe Val Lys Glu Gln Leu
                    340         350             360             370

380                     390             400             410             420             430
AGT CTG CTG GAC AGG TTC ACG GAG GAT GCC AAG AGG CTG CGT CTG CGT CTG CGG CTG TAT GGC TCC GAG GCC
Ser Leu Leu Asp Arg Phe Thr Glu Asp Ala Lys Arg Leu Arg Leu Arg Leu Arg Leu Tyr Gly Ser Glu Ala 440             450             460             470             480
TTT GCC ACT GAC TTT CAG GAC TCA GCT GCA GCT AAG AAG CTC ATC AAC GAC TAC
Phe Ala Thr Asp Phe Gln Asp Ser Ala Ala Ala Lys Lys Leu Ile Asn Asp Tyr 490             500             510             520             530             540
GTG AAG AAT GGA ACT AGG GGG AAA ATC ACA GAT CTG ATC AAG GAC CTT GAC TCG
Val Lys Asn Gly Thr Arg Gly Lys Ile Thr Asp Leu Ile Lys Asp Leu Asp Ser 550             560             570             580             590
CAG ACA ATG GTC ATG GTC CTG AAT TAC ATC TTC TTT AAA GCC AAA TGG GAG ATG
Gln Thr MET MET Val MET Val Leu Asn Tyr Ile Phe Phe Lys Ala Lys Trp Glu MET 600             610             620             630             640
CCC TTT GAC CCC CAA GAT ACT CAT CAG TCA AGG TTC TAC TTG AGC AAG AAA AAG
Pro Phe Asp Pro Gln Asp Thr His Gln Ser Arg Phe Tyr Leu Ser Lys Lys Lys
```

*Fig. 1b*

```
650           660           670           680           690        700
 |             |             |             |             |          |
TGG GTA ATG GTG CCC ATG ATG AGT TTG CAT CAC CTG ACT ATA CCT TAC TTC CGG
Trp Val MET Val Pro MET MET Ser Leu His His Leu Thr Ile Pro Tyr Phe Arg 710           720           730           740           750
 |             |             |             |             |
GAC GAG GAG CTG TCC TGC ACC GTG GAG CTG GTG GAG CTG AAG TAC ACA GGC AAT GCC AGC
Asp Glu Glu Leu Ser Cys Thr Val Glu Leu Val Glu Leu Lys Tyr Thr Gly Asn Ala Ser 760           770           780           790           800        810
 |             |             |             |             |          |
GCA CTC TTC ATC CTC CCT GAT CAA GAC AAG ATG GAG GAC AAG GAA GTG GAA GCC ATG CTG
Ala Leu Phe Ile Leu Pro Asp Gln Asp Lys MET Glu Asp Lys Glu Val Glu Ala MET Leu 820           830           840           850           860
 |             |             |             |             |
CTC CCA GAG ACC CTG AAG CGG TGG AGA GAC TCT CTG GAG TTC AGA GAG ATA GGT
Leu Pro Glu Thr Leu Lys Arg Trp Arg Asp Ser Leu Glu Phe Arg Glu Ile Gly 870           880           890           900           910
 |             |             |             |             |
GAG CTC TAC CTG CCA AAG TTT TCC ATC TCG AGG GAC TAT AAC GAC ATA
Glu Leu Tyr Leu Pro Lys Phe Ser Ile Ser Arg Asp Tyr Asn Asp Ile 920           930           940           950           960        970
 |             |             |             |             |          |
CTT CTC CAG CTG GGC ATT GAG GAA GCC TTC ACC AGC AAG GCT GAC CTG TCA GGG
Leu Leu Gln Leu Gly Ile Glu Glu Ala Phe Thr Ser Lys Ala Asp Leu Ser Gly
```

*Fig. 1c*

```
ATC ACA GGG GCC AGG AAC CTA GCA GTC TCC CAG GTG GTC CAT AAG GCT GTG CTT
Ile Thr Gly Ala Arg Asn Leu Ala Val Ser Gln Val Val His Lys Ala Val Leu

GAT GTA TTT GAG GAG GGC ACA GAA GCA TCT GCT GCC ACA GCA GTC AAA ATC ACC
Asp Val Phe Glu Glu Gly Thr Glu Ala Ser Ala Ala Thr Ala Val Lys Ile Thr
                                        349 350

CTC CTT TCT GCA TTA GTG GAG ACA ATT GTG CGT TTC AAC AGG CCC TTC
Leu Leu Ser Ala Leu Val Glu Thr Ile Val Arg Phe Asn Arg Pro Phe
P₁ P₁ P₁'                          368 369

CTG ATG ATC ATT GTC CCT ACA GAC ACC CAG AAC ATC TTC TTC ATG AGC AAA GTC
Leu MET Ile Ile Val Pro Thr Asp Thr Gln Asn Ile Phe Phe MET Ser Lys Val

ACC AAT CCC AAG CAA GCC TAG AGC TTG CCA TCA AGC AGT GGG GCT CTC AGT AAG
Thr Asn Pro Lys Gln Ala --- Ser Leu Pro Ser Ser Ser Gly Ala Leu Ser Lys
```

*Fig. 1d*

```
1250                    1260                    1270                    1280                    1290
 |                       |                       |                       |                       |
GAA CTT GGA ATG CAA GCT GGA TGC CTG CTC TGG CAC AGC CTG GCC CCT GTG
Glu Leu Gly MET Gln Ala Gly Cys Leu Leu Trp His Ser Leu Ala Pro Val 1300                    1310                    1320                    1330                    1340                    1350
 |                       |                       |                       |                       |                       |
CAC CGA GTG GCC ATG GCA GTG GCC CTG TCT GCT TAT CCT TGG AAG GTG ACA
His Arg Val Ala MET Ala Val Ala Leu Ser Ala Tyr Pro Trp Lys Val Thr 1360                    1370                    1380                    1390                    1400
 |                       |                       |                       |                       |
GCG ATT CCC TGT GTA GCT CTC ACA TGC ACA GGG GCC CAT GGA CTC TTC AGT CTG
Ala Ile Pro Cys Val Ala Leu Thr Cys Thr Gly Ala His Gly Leu Phe Ser Leu 1410                    1420
 |                       |
GAG GGT CCT GGG CCT CCT GGA ATT
Glu Gly Pro Gly Pro Pro Gly Ile
```

Fig. 1e

α-1-ANTICHYMOTRYPSIN ANALOGUES HAVING ELASTASE INHIBITORY ACTIVITY

REFERENCE TO RELATED APPLICATIONS

The present application is a continuation-in-part of U.S. patent application Ser. No. 08/005,898, and U.S. patent application Ser. No. 08/005,908, U.S. Pat. No. 5,357,064, filed Jan. 15, 1993, which are divisionals of U.S. patent application Ser. No. 07/735,322, filed Jul. 24, 1991, now U.S. Pat. No. 5,266,465, which is in turn a divisional application of U.S. patent application Ser. No. 07/370,704 filed Jun. 23, 1989, which is now U.S. Pat. No. 5,079,336. The disclosures of each of these applications is hereby incorporated by reference.

REFERENCE TO GOVERNMENT GRANTS

The work for the present invention was supported in part by National Institutes of Health grant AG-10599 and AR-39674. The United States government may have certain rights in the invention.

FIELD OF THE INVENTION

The present invention relates to the field of protein produced by recombinant DNA technology. More particularly the present invention relates to proteins capable of inhibiting elastase.

BACKGROUND OF THE INVENTION

Antichymotrypsin (ACT) and α1 protease inhibitor (α1-PI) are members of the serine protease inhibitor superfamily and have closely related primary amino acid sequences and three dimensional structures. Antichymotrypsin, however, has a narrower spectrum of inhibitory activity. In particular, α1-PI is a very effective inhibitor of human neutrophil elastase (HNE), whereas antichymotrypsin is a substrate for and is inactivated by, this enzyme. Potempa, et al., *J. Biol. Chem.*, 1991, 266, 21482.

It is well recognized that human neutrophil elastase plays a significant role in mediating a number of molecular and cellular mechanisms of inflammation, Travis and Fritz, *Am. Rev. Resp. Dis.* 1991, 43, 1412.

Some mediators of inflammation appear to be regulated by proteases and protease inhibitors. One example is tumor necrosis factor (TNF)-enhanced platelet activation through a TNF-mediated release of cathepsin G (catG) from neutrophils; an effect that was blocked by antichymotrypsin, ACT. Renesto, P. et al., *J. Immunol.*, 1991, 146, 2305. The synthesis and release of leukotriene B4 (LTB4) and platelet activating factor (PAF) from TNF-stimulated neutrophils was blocked by alpha-1-proteinase inhibitor (α1PI) and ACT and enhanced by catG and human neutrophil elastase (HNE). Camussi, G. et al., *J. Exp. Med.*, 1988, 168, 1293 and Camussi, G. et al., *Eur. J. Biochem.*, 1989, 182, 661.

The vascular and tissue microenvironment of an inflammatory reaction can serve to modify an effective response by restricting access of endogenous or administered anti-inflammatory agents. For example, secretory leukocyte protease inhibitor (SLPI), a small (11.7 kD) basic polypeptide, appears to be able to gain access to the subjacent microenvironment of an adherent neutrophil and protect local tissue from proteolysis by neutrophil granule elastase. An elastase specific chloromethyl ketone inhibitor, but not α1PI, serum or plasma, inhibited neutrophil-mediated endothelial damage, in vitro, in a model of human microvascular injury. Nathan showed that adherent neutrophils generate free radical oxygen with distinctly different kinetics than neutrophils in suspension. Nathan, *J. Clin. Invest.*, 1980, 80, 1550. It is not known if highly reactive free radical oxygen species and their products accumulate between adherent neutrophils and the subjacent tissue.

Human neutrophils contain two distinct classes of granules distinguished by histochemistry and ultrastructural cytochemistry. Bainton, et al., *J. Cell Biol*, 1968, 39, 286 and Bainton, et al., *J. Cell Biol.*, 1968, 39, 299. The azurophil (or primary) granules are usually large, dense and contain myeloperoxidase (MPO) and neutral proteases. The smaller, less-dense, specific (or secondary) granules, are peroxidase-negative and contain lysozyme and lactoferrin. Weinbaum and colleagues have described at least three distinct populations of azurophil granules within the neutrophil. One population has all the elastase antigen, but little MPO activity. The azurophil granules are heterogeneous and respond differently to degranulation stimuli. The specific granules are also heterogeneous with different sensitivities to calcium-induced release of lactoferrin. The selective inhibition of protein kinase C does not inhibit azurophil degranulation but inhibits the release of specific granule contents. Thus, multiple and coordinated signals may be required to stimulate the release of human neutrophil elastase, catG and proteinase 3 from neutrophils in the microenvironment that characterizes the inflammatory response. The kinetics of binding and responding to the signals may also be important in regulating the physiologic response to inflammation. Release of human neutrophil elastase in the lung has been found to occur within the alveolar interstitium, well after the neutrophil has left the circulation. Little is known about neutrophil degranulation during the process of diapedesis. Respiratory epithelial cells respond to human neutrophil elastase by increased IL-8 expression and IL-8, in turn, mediates migration through epithelial cells. Therefore a dynamic and destructive cycle of neutrophil recruitment accompanied by release of HNE followed by accentuated neutrophil migration is established.

Release of neutrophil proteases by adherent cells is not well studied, although it is known that phorbol myristate acetate (PMA) stimulation of neutrophils results in release of a protease that digests the subjacent extracellular matrix. Campbell, et al., *J. Clin. Invest.*, 1982, 70, 845 and Weiss, et al., *J. Immunol.*, 1986, 136, 636. Neutrophils adherent to matrix proteins (e.g., laminin, fibronectin or vitronectin were stimulated by physiological signals such as TNF or granulocyte colony stimulating factor (G-CSF) whereas suspended cells were not. Adherent cells expressed a respiratory burst that was 10- to 50-fold more sensitive to TNF and G-CSF than to PMA and 50- to 250-fold more sensitive than to fMet-Leu-Phe or C5a. In addition, they responded with markedly different kinetics than suspended cells.

Accordingly, inhibitors of proteolytic enzymes, when administered therapeutically may limit the molecular and cellular mechanisms of inflammation, thus reducing tissue damage. Therefore, there remains a need for safe and effective elastase inhibitors for clinical applications in animals. Therapeutic agents based on multifunctional protease inhibitors will clinically advance therapy of diseases where free radicals as well as proteases have been implicated in the mechanism of injury such as the adult respiratory syndrome, pancreatitis, inflammatory skin lesions and reperfusion injury.

SUMMARY OF THE INVENTION

The present invention provides analogues of human α-1-antichymotrypsin which are efficient inhibitors of human neutrophil elastase. The α-1-antichymotrypsin analogues of the present invention are manipulated such that they cease being a substrate for human neutrophil elastase and become inhibitors of human neutrophil elastase. The present invention provides for analogues of human α-1-antichymotrypsin wherein the amino acid leucine at position 358 is substituted with an amino acid selected from the group consisting of methionine, isoleucine, valine, alanine, aspartic acid, threonine, and glutamic acid. The analogues may further have proline at least one of amino acid positions 356, 357, 359, 360 and 361. The analogues of the present invention include human α-1-antichymotrypsin produced from a nucleotide sequence, wherein the amino acids corresponding to Thr—Leu—Leu—Ser—Ala—Leu (SEQ ID NO: 7) at amino acid positions 356 through 361 of wild-type antichymotrypsin are substituted with Ile—Pro—Xxx—Ser—Ile—Pro (SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine.

A further aspect of the invention provides novel antichymotrypsin polypeptides. The novel polypeptide of the invention is produced from the nucleotide sequence encoding the entire amino acid sequence of mature human wild type α-1-antichymotrypsin, see FIG. 1, with amino acid positions 356 through 361 substituted with Ile—Pro—Xxx—Ser—Ile—Pro (SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine.

The present invention also provides analogues of human wild type α-1-antichymotrypsin produced from a nucleotide sequence wherein amino acids, Ala—Ala, corresponding to positions 349 and 350 are changed to Gly—Thr and amino acid, Val, at position 368, is substituted with Thr. Novel polypeptides analogues of α-1-antichymotrypsin, having the substitutions set forth above, are also subjects of the present invention.

Further, amino acid substitutions at positions 356 through 361 and amino acid substitutions at positions 349, 350, and 368, may occur within the same nucleotide and amino acid sequences to yield additional novel analogues of α-1-antichymotrypsin.

The novel polypeptides of the invention include N-terminal extensions, Met—Ala—Ser—Leu—Cys—His—Pro (SEQ ID NO: 5), and Met—Ala—Ser, either of which may independently be added to the wild type α-1-antichymotrypsin and the novel α-1-antichymotrypsin analogues of the present invention. The nucleotide sequences coding for the N-terminal extensions and α-1-antichymotrypsins having the N-terminal extensions are within the scope of the present invention.

The present invention also provides nucleic acid sequences encoding the α-1-antichymotrypsin analog of the invention, expression vectors comprising the nucleic acid sequence, transformed host cells capable of expressing the nucleic acid sequences of the invention, cell cultures capable of expressing the analogues of human α-1-antichymotrypsin of the present invention and protein preparations comprising the analogues of human α-1-antichymotrypsin of the invention.

A further aspect of the present invention provides methods of producing analogues of human α-1-antichymotrypsin comprising culturing a host cell capable of expressing an analogue of human α-1-antichymotrypsin to produce cells containing an analogue of human α-1-antichymotrypsin. Optionally, the mixture of cells and medium containing the analogues of human α-1-antichymotrypsin can be purified to produce the analogues of human α-1-antichymotrypsin in purified form.

An additional aspect of the invention provides a method of inhibiting neutrophil elastase comprising contacting the elastase with an inhibitory amount of an analogue of human α-1-antichymotrypsin of the invention.

This invention is more particularly pointed out in the appended claims and is described in its preferred embodiments in the following description.

BRIEF DESCRIPTION OF THE FIGURES

FIGS. 1A–1E show the complete nucleotide sequence and predicted amino acid sequence of human wild type α-1-antichymotrypsin. The full length gene is encoded by nucleotide residues 1-1209.

DETAILED DESCRIPTION OF THE INVENTION

Applicants have unexpectedly and surprisingly found that substitutions of certain amino acids in the sequence coding for human α-1-antichymotrypsin changes α-1-antichymotrypsin from a substrate for human neutrophil elastase to an efficient inhibitor of human neutrophil elastase while retaining the ability to inhibit chymotrypsin.

The present invention provides a nucleotide sequence of human wild type α-1-antichymotrypsin, FIG. 1, wherein the amino acids corresponding to Thr—Leu—Leu—Ser—Ala—Leu (SEQ ID NO: 7) at amino acid positions 356 through 361 of wild-type α-1-antichymotrypsin are substituted with Ile—Pro—Xxx—Ser—Ile—Pro (SEQ ID NO: 8). The novel polypeptide sequence coding for the substitutions at amino acid positions 356 to 361 is also included in the present invention.

A nucleotide sequence analogue of human wild type α-1-antichymotrypsin having nucleotides coding for substitutions at the corresponding amino acid positions 349, 350 and 368 is provided for in the present invention. The nucleotides in these positions in the analogue code for Gly, Thr, and Thr, respectively. A polypeptide sequence having these substitutions is also within the scope of the invention.

The analogue of the present invention, wherein the amino acids corresponding to alanine-alanine at positions 349 and 350 of wild type α-1-antichymotrypsin are substituted with glycine-threonine respectively, form a Kpn I restriction endonuclease site and the amino acids corresponding to valine-arginine at positions 368 and 369 of wild type antichymotrypsin are substituted with threonine-arginine respectively form a Mlu I restriction endonuclease site, exhibits elastase inhibitory activity.

N-terminal extensions may be added to the novel analogues of the present invention, or to wild type α-1-antichymotrypsin. These N-terminal extensions include the nucleotide sequences for the polypeptide sequences Met—Ala—Ser—Leu—Cys—His—Pro (SEQ ID NO: 5) and Met—Ala—Ser.

The analogues of the present invention were used to analyze the nature of the interaction between serine protease inhibitors and serine proteases. Residues in the P1 position of the reactive center and around the reactive center of antichymotrypsin resulted in stable complex formation between elastase and α-1-antichymotrypsin analogues of the present invention.

The amino acid sequence Ile—Pro—Xxx—Ser—Ile—Pro (SEQ ID NO: 8) that is substituted into wild type antichymotrypsin was selected from the corresponding segment of α-1-proteinase inhibitor, i.e. the reactive center of proteinase inhibitor from the P3 through the P3' positions. The nomenclature employed herein is consistent with that described by Schechter and Berger, incorporated herein by reference. Schechter and Berger, *Biochem. Biophys. Res. Commun.*, 1967, 27, 157. Wild type α-1-antichymotrypsin refers to the native, mature form of human α-1-antichymotrypsin.

α-1-proteinase inhibitor, in which Met—Ser are the P1-P1' residues, inhibits HNE with a second order rate constant of $10 \times 10^6$ $M^{-1}$. α-1-antichymotrypsin is highly homologous to 1-proteinase inhibitor with 44.5% identical residues in the corresponding positions. However, the sequences flanking the P1-P1'Leu—Ser residues at the reactive center are quite different. Wild type α-1-antichymotrypsin, while an excellent inhibitor of chymotrypsin, is not an efficient inhibitor of HNE. In fact, HNE cleaves α-1-antichymotrypsin at least at position P4-P3 (Ile355 - Thr356), producing inactivation of its inhibitory properties.

Thus, the present invention, by changing only a small portion of human α-1-antichymotrypsin, surprisingly changes its specificity such that it is an efficient inhibitor of a completely different enzyme, namely elastase, while retaining the ability of the α-1-antichymotrypsin analogue to inhibit chymotrypsin.

Generally, the α-1-antichymotrypsin analogues of the invention are produced in host cells that have been transformed with an expression vector comprising a nucleic acid sequence coding for a particular protein. The transformed cells are cultured under conditions whereby the nucleic acid sequence coding for the particular protein is expressed. After a suitable amount of time for the protein to accumulate, the protein is purified from the transformed cells.

A human gene coding for α-1-antichymotrypsin can be readily obtained from a human liver cDNA library. Suitable libraries can be obtained from commercial sources such as Clontech, Palo Alto, Calif. Positive clones are then subjected to DNA sequencing to determine the presence of a DNA sequence coding for α-1-antichymotrypsin. DNA sequencing is readily accomplished using the chain termination method of Sanger et al., *Proc. Nat'l. Acad. Sci, U.S.A.*, 1977, 74, 5463. The DNA sequence coding for α-1-antichymotrypsin is then inserted into an expression vector for later expression in a host cell.

The analogue of α-1-antichymetrypsin of the invention may be prepared using the α-1-antichymotrypsin cassette analogue disclosed in U.S. Pat. No. 5,079,336, the disclosures of which are hereby incorporated by reference. For example, a DNA sequence encoding amino acids substitutions at positions 356 through 361 Ile—Pro—Xxx—Ser—Ile—Pro (SEQ ID NO: 8) is inserted into the cassette, which is then inserted into the sequence encoding α-1-antichymotrypsin. In addition, the DNA sequence encoding the protein having amino acid substitutions at positions 356-361, and the DNA sequence encoding the polypeptide having amino acid substitutions at positions 349, 350, and 368 may be prepared by a cassette vector. Alternatively, a DNA sequence encoding an analogue of antichymotrypsin may be prepared by PCR. Ultimately, a polypeptide analogue of α-1-antichymotrypsin may be produced.

Expression vectors and host cells are selected to form an expression system capable of synthesizing α-1-antichymotrypsin or analogue. Host cells suitable for use in the invention include prokaryotic and eukaryotic cells that can be transformed to stably contain and express α-1-antichymotrypsin, as disclosed in U.S. Pat. No. 5,079,336, incorporated herein by reference. For example, nucleic acid coding for recombinant α-1-antichymotrypsin or analogue may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serfaria marcescens*, various species of *Pseudomonas*, or other bacterial strains.

Commonly used eukaryotic systems include yeast, such as *Saccharomyces cerevisiae*; insect cells, such as *Spodoptera frugiperda*; chicken cells, such as E3C/O and SL-29; mammalian cells, such as HeLa, Chinese hamster ovary cells (CHO), COS-7 or MDCK cells and the like. The foregoing list is illustrative only and is not intended in any way to limit the types of host cells suitable for expression of the nucleic acid sequences of the invention. As used herein, expression vectors refer to any type of vector that can be manipulated to contain a nucleic acid sequence coding for recombinant α-1-antichymotrypsin, such as plasmid expression vectors and vital vectors. The selection of the expression vector is based on compatibility with the desired host cell such that expression of the nucleic acid coding for recombinant α-1-antichymotrypsin results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol or kanamycin resistance.

Suitable expression vectors, promoters, enhancers, and other expression control elements are known in the art and may be found in Sambrook et al., *Molecular Cloning: A Laboratory Manual*, second edition, Cold Spring Harbor Laboratory Press, Cold Spring Harbor, N.Y. (1989). For example, plasmids such as pBR322, pUC18, pUC19, pZMS, pZM, and the plasmids described in the Examples herein may be used for expression in *E. coli*. Plasmids YRp7 may be used for expression in *S. cervisiae*. Plasmids such as pMT2 and pMSG may be used for expression in mammalian cells. Suitable viral vectors include baculovirus, *Vaccinia* virus and adenovirus.

For expression of α-1-antichymotrypsin or analogues in *E. coli*, a gene expression system based on bacteriophage T7 RNA polymerase as disclosed in Studier and Moffatt, *J. Mol. Biol.*, 1986, 189, 113, which is specifically incorporated as if fully set forth herein, may be used. In this system, *E. coli* cells transformed with plasmids containing the bacteriophage T7 promoter operatively linked with a DNA sequence coding for a selected product are infected with lambda phage having an expressible gene for T7RNA polymerase. The cells are infected with phage after sufficient copies of the plasmids are present in the host cells and protein synthesis begins soon after infection.

The expression vector preferably comprises at least one transcription and translation control element operatively linked to the nucleic acid sequence coding for human α-1-antichymotrypsin. For example, in an upstream position, a promoter may be followed by a translation initiation signal, comprising a ribosome binding site and an initiation codon, and in a downstream position may be a transcription termination signal. The transcription and translation control elements may be ligated in any functional combination or order. The transcription and translation control elements used in any particular embodiment of the invention will be chosen with reference to the type of cell into which the expression vector will be introduced, so that an expression system is created. Introduction of the expression vector incorporating a nucleic acid sequence coding for α-1-antichymotrypsin or analogue into a host cell can be performed in a variety of ways known in the art, such as calcium chloride or lithium chloride co-precipitation or electropotation.

E. coli is a presently preferred host cell for expression of α-1-antichymotrypsin or analogue. Cloning and expression can be obtained rapidly in E. coli. Production in E. coli is readily amenable to cost-effective, large scale fermentation and protein purification.

Transformed host cells containing a DNA sequence coding for human α-1-antichymotrypsin analogues may then be grown in an appropriate medium for the host. Where an inducible promoter is employed, the host cell may be grown to high density and the promoter turned on for expression of α-1-antichymotrypsin or analogue. Where the promoter is not inducible, then constitutive production of the protein product will occur. Constitutive production of the α-1-antichymotrypsin analogue is preferable in expressions systems where it is not substantially toxic to the host cell. The cells are then grown until product accumulation reaches desired levels at which time the cells are then harvested and the protein product purified in accordance with conventional techniques. Suitable purification methods include, but are not limited to, ion exchange chromatography, affinity chromatography, electrophoresis, dialysis and other methods of protein purification known in the art.

Thus, the present invention provides a method of producing human α-1-antichymotrypsin or analogue comprising culturing a host cell capable of expressing human α-1-antichymotrypsin or analogue to produce cells containing human α-1-antichymotrypsin or analogue and optionally purifying the mixture to produce human α-1-antichymotrypsin or analogue in a purified form.

Protein preparations, of purified or unpurified recombinant α-1-antichymotrypsin analogue produced by host cells, are accordingly produced which comprise α-1-antichymotrypsin and other material such as host cell components and/or cell medium, depending on the degree of purification of the protein.

The term "purified", when used to describe the state of nucleic acid sequences of the invention, refers to nucleic acid sequences substantially free of nucleic acid not coding for human α-1-antichymotrypsin or other materials normally associated with nucleic acid in non-recombinant cells, i.e., in its "native state".

The term "purified" or "in purified form" when used to describe the state of α-1-antichymotrypsin protein or analogue protein, refers to α-1-antichymotrypsin or analogue free, to at least some degree, of cellular material or other material normally associated with it in its native state. Preferably α-1-antichymotrypsin or analogue has a purity (homogeneity) of at least about 25% to about 100%. More preferably the purity is at least about 50%.

The α-1-antichymotrypsin, analogues and protein preparations of the invention are expected to be useful for treatment of septic shock, pancreatitis, coagulation disorders, liver diseases, certain diseases caused by microbes that penetrate the skin byelaborating a microbial chymotrypsin-like enzyme and skin inflammation in mammals, including humans. The compositions of the invention may be administered to mammals, including humans by various routes, including intravenous, intramuscular and intraperitoneal routes, and topically to an affected area of the skin. The compositions of the invention may be useful in the treatment of diseases such as but not limited to the following: rheumatoid arthritis; glomerulonephritis; lung diseases such as adult respiratory distress syndrome and emphysema; reperfusion injuries to cardiac and cerebral tissue and injuries as a result of transplants; aging; sepsis; pancreatitis; co-administration with chemotherapeutic agents such as adriamycin; and in prevention of ionizing radiation side effects such as skin problems, mucositis, and hair loss.

Thus, the present invention provides a method of inhibiting elastase comprising contacting elastase with an inhibitory amount of the analogue of human α-1-antichymotrypsin wherein the amino acids corresponding to Thr—Leu—Leu—Ser—Ala—Leu (SEQ ID NO: 7) at amino acid positions 356 through 361 of wild-type α-1-antichymotrypsin are substituted with Ile—Pro—Xxx—Ser—Ile—Pro (SEQ ID NO: 8), or contacting elastase with an inhibitory amount of a protein preparation of the invention.

In addition, the invention further provides a method of using the analogue of human α-1-antichymotrypsin wherein the amino acids corresponding to Thr—Leu—Leu—Ser—Ala—Leu (SEQ ID NO: 7) at amino acid positions 356 through 361 of wild-type α-1-antichymotrypsin are substituted with ile—Pro—Xxx—Ser—Ile—Pro (SEQ ID NO: 8) to inhibit elastase activity comprising the step of contacting elastase with an amount of such α-1-antichymotrypsin analogue effective to inhibit the elastase.

The terms "effective amount" and "inhibitory amount" refer to concentrations of the α-1-antichymotrypsin analogue of the invention that reduce the activity of elastase upon natural or synthetic substrates.

The analogues of α-1-antichymotrypsin of the present invention exhibit neutrophil elastase inhibitory activity and are useful in the same manner as native or wild-type antichymotrypsin. The analogues are useful as inhibitors of neutrophil elastase, and in the treatment and prevention of reperfusion injury, inflammation of the lungs, inflammatory bowel disease, skin inflammation, pancreatitis, glomerulonephritis, and sepsis.

In the case of lung inflammation, inflammation may be caused by aspiration of an acidic substance such as and not limited to stomach contents, smoke, infection, such as pathogen infection including infection from a gram negative bacterium (Escherichia and Pseudomonas, for example). In regard to reperfusion injury, the analogues of the invention may be administered to prevent injury during perfusion to remove or dissolve a blood clot.

The analogues of the invention may be administered with a pharmaceutically-acceptable carrier or diluent, such as a saline solution or other buffer. Suitable pharmaceutical carriers are well known in the art and are described for example, in Gennaro, Alfonso, ed., Remington's Pharmaceutical Sciences, 18th Edition, 1990, Mack Publishing Co., Easton Pa., a standard reference text in this field. Carriers may be selected with regard to the intended route of administration and the standard pharmaceutical practice. Dosages will be set with regard to weight, and clinical condition of the patient. The proportional ratio of active ingredient to carrier will naturally depend on the chemical nature, solubility, and stability of the analogues, as well as the dosage contemplated.

The analogues of the invention may be employed in the method of the invention singly or in combination with other compounds, including and not limited to other analogues of the invention. The method of the invention may also be used in conjunction with other treatments including and not limited to antibodies, toxins, and antisense oligonucleotides. For in vivo applications the amount to be administered will also depend on such factors as the age, weight, and clinical condition of the patient. The analogues of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the analogues, medicaments, and compositions of the present invention, may determine the sites in the organism to which the analogue may be delivered. For instance, topical application may be administered in creams, ointments, gels, oils, emulsions, pastes, lotions, and the like. For parenteral administration, the analogues may be used in the form of a sterile aqueous solution which may contain other solute, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added.

Methods of inhibiting neutrophil elastase, treating skin inflammation, lung inflammation, glomerulonephritis, pancreatitis, sepsis, inflammatory bowel disease, and treating and preventing reperfusion injury are also provided whereby an α-1-antichymotrypsin analogue having amino acid substitutions at position 358, or positions 356–361 with position 358 selected from the amino acids identified above; or wherein the amino acids of human wild type α-1-antichymotrypsin Thr—Leu—Leu—Ser—Ala—Leu corresponding to positions 356–361 are substituted with Ile—Pro—Xxx—Ser—Ile—Pro; is added to a sample exhibiting the condition to be treated.

The present invention also provides pharmaceutical compositions comprising the α-1-antichymotrypsin analogue of the invention and a pharmaceutically acceptable carrier or diluent.

The compositions of the invention are preferably delivered to the affected mammal in combination with a physiologically acceptable carrier or diluent, such as a saline solution or other buffer. Suitable pharmaceutical carriers are well known in the art and described, for example, in Remington's Pharmaceutical Sciences, E. W. Martin, a standard reference text in this field. For treatment of skin inflammation the compositions of the invention may be applied to the affected area in combination with a physiologically acceptable ointment or cream. The particular amount of the compositions of the invention that will be administered to the mammal for any particular condition will depend on the type of illness, and other factors such as the weight and age of the patient and route of delivery. For topical applications, the compositions of the invention are applied in an amount effective to reduce or inhibit worsening of skin inflammation.

EXAMPLES

Production and Purification of Recombinant α-1-Antichymotrypsin Analogues

Materials

Chymotrypsin was obtained from Sigma or Boehringer-Mannheim. All chromophoric protease substrates were obtained from Bachem, as was phenylmethylsulfonyl fluoride (PMSF).

Human serum α-1-antichymotrypsin was prepared using a procedure based on the work of Tsuda et al., Tokai, *J. Exp. Clin. Med.*, 1982, 7, 201. This method affords pure α-1-antichymotrypsin in three steps, batchwise elution from DNA cellulose, G-150 chromatography and CaCl gradient elution from DNA cellulose.

Plasmid constructions and DNA manipulations were carried out following Sambrook et al., *Molecular Cloning: A Laboratory Manual*, second edition, Cold Spring Harbor Laboratory Press, Cold Spring Harbor, N.Y. (1989).

Identification and Sequencing of the Gene from Human Antichymotrypsin

A human liver cDNA library in the phage expression vector lambda-gtll provided by Mitchell Weiss, Department of Human Genetics, University of Pennsylvania, was screened according to the method of Young and Davis, *Proc. Natl. Acad. Sci., U.S.A.*, 1977, 74, 5463, with polyclonal antisera raised against C1 esterase inhibitor (DAKO, Santa Barbara, Calif.), a related serine protease inhibitor. Positive clones were picked, rescreened and plaque-purified. DNA sequencing was performed with the chain termination method of Sanger et al., *Proc. Natl. Acad. Sci.*, 1977, 74, 5463, using oligonucleotide primers obtained from the Nucleic Acid Synthesis Center of the Wistar Institute (Philadelphia, Pa.).

The DNA sequence and the derived amino acid sequence of the EcoR1 fragment from one of the positive lambda-gt11 cDNA clones contained the entire coding region of the mature human α-1-antichymotrypsin, as depicted in FIG. 1. The construct also included a 21 nucleotide extension of the 5'-end encoding 7 amino acids, comprising the sequence 5'-Met—Ala—Ser—Leu—Cys—His—Pro— (SEQ ID NO: 5). The mature protein contains 398 amino acids ($M_r$ 45,031) starting from amino acid position 1, Asn, at the amino terminus and contains a single cysteine residue at position 236.

Preparation of α-1-antichymotrypsin Having Substitutions at Amino Acid Positions 356–361 by PCR An analogue of α-1-antichymotrypsin having substitutions at amino acid positions 356–361 was prepared by PCR. The commercially available plasmid pKC30 was cut by BamHI and the staggered ends were filled by Klenow reaction. The linearized plasmid with both ends blunt ended was self ligated, and *E. coli* N4830-1 was transformed by the ligation reaction mixture. The plasmid purified from transformants was pKC30(-BamHI), indicating pKC30 with the only BamHI site removed. This pKC30(-BamHI) was digested by HpaI, and created two blunt ends for the next ligation step.

Using XbaI and EcoRV, a 0.2 kb fragment containing a ribosome binding site was cut out of the plasmids pAR3038, pAR3039, and pAR3040. The EcoRV cut created a blunt end. The staggered end created by XbaI was filled by the Klenow reaction. With both ends blunted, the three 0.2 kb fragments were separately ligated to HpaI digested pKC30 (-BamHI). The three ligation mixtures were used to transform N4830-1 separately.

Three vectors were obtained from these transformants. They were named pZM3038, pZM3039, and pZM3040, corresponding to three reading frames. These pZM vectors contained a pL promoter from pKC30, and received Shine-Delgarno sequences from pAR vectors. The unique cloning site of these vectors is BamHI which is located in the fragment from pAR.

One of pZM3038, pZM3039, or pZM3040 was cut by NheI, and produced two fragments of about 5.9 kb, and about 0.75 kb. The 5.9 kb fragment was gel purified and ligated to recircularize. N4830-1 was transformed with this ligation reaction. The plasmid isolated from the transformants was named pZMs. pZMs has a unique cloning site, NheI, which is downstream from the pL promoter, Shine-Delgarno sequence, and the start codon.

Primers 1, 2, 3, and 4, as shown in Table 1, were prepared by standard techniques set forth in Sambrook et al., *Molecular Cloning: A Laboratory Manual*, second edition, Cold Spring Harbor Laboratory Press, Cold Spring Harbor, N.Y. (1989) and used in a polymerase chain reaction (PCR) protocol to introduce bases coding for P3-P3' into the sequence coding for α-1-antichymotrypsin. Standard PCR protocols are known to those skilled in the art.

The full-length nucleotide sequence was created in two parts, Fragments A and B, which were combined to produce the full-length nucleotide sequence.

To construct Fragment A, two primers were used. Primer 1 contains the 5' sequence of the coding or sense strand for α-1-antichymotrypsin with an extended 5' tail which contains an NheI cloning site, which is shown underlined in Table 1. Primer 2 comprises bases corresponding to amino acids extending toward the N terminus. Primers 1 and 2 were then used with the polymerase chain reaction and the sequence coding for this part of α-1-antichymotrypsin was subcloned in pUC19 to produce Fragment A.

Standard PCR methods were followed for the production of Fragment A. 1 µl (100 ng/µl) of Primer 1 and 1 µl (100 ng/µl) of Primer 2, 10 µl of 10× PCR buffer, 10 µl of 2 mM dNTP and 0.5 µl of Taq enzyme were added to 10 ng of template DNA, pUC19 containing the α-1-antichymotrypsin gene, with distilled water bringing the reaction volume to 100 µl. Three steps of PCR were performed, 94° C. for 15 seconds, 52° C. for 15 seconds, and 72° C. for 1 second. The three steps equal one cycle, thirty cycles were run.

To construct Fragment B, two different primers were used. Primer 3 comprises bases corresponding to amino acids extending toward the C terminus. Primer 4 contains an extended 5' tail that contains an NheI cloning site, which is shown underlined in Table 1. Primers 3 and 4 were then used with the polymerase chain reaction and this part of the sequence coding for α-1-antichymotrypsin was subcloned in pUC19 to produce fragment B. The PCR protocol set forth above for the production of Fragment A was also followed for the production of Fragment B.

The full-length sequence was then produced by the protocol set forth above for Fragment A, with the substitution of 5–10 ng of each of Fragment A and Fragment B. The fragments were denatured and reannealed. The fragments were reannealed to produce heteroduplexes of Fragments A and B overlapping at a sequence coding for positions 356–361 that was created via Primers 2 and 3. The heteroduplexes of Fragments A and B were extended using Taq DNA polymerase with the overlapping portions of Fragments A and B serving as primers to produce the full-length sequence coding for α-1-antichymotrypsin having Ile—Pro—Met—Ser—Ile—Pro (SEQ ID NO: 8) in place of Thr—Leu—Leu—Ser—Ala—Leu (SEQ ID NO: 7) of the wild-type. The full-length sequences were then amplified using Primers 1 and 4.

The amplified full-length sequence was then digested with NheI and inserted into the expression vector pZMs, which was digested with NheI. E. coli was then transformed with pZMs containing the full length gene. As such, analogues of antichymotrypsin with altered amino acid positions 356–361 were expressed. This analogue is represented herein as rACT-P3-P3'PI. Other analogues of human wild type α-1-antichymotrypsin of the present invention may be similarly prepared.

TABLE 1

| Primer | Sequence | SEQ ID NO: |
|---|---|---|
| 1 | 5'-CCCCATATGGCTAGCAACAGCCCACTTG-3' | 1 |
| 2 | 5'-CCACAGGAATAGACATTGGAATGATTTTGACTGCTGTGG-3' | 2 |
| 3 | 5'-CATTCCAATGTCTATTCCTGTGGAGACAAGGACCAT-3' | 3 |
| 4 | 5'-TTTCATATGGCTAGCGCTCTAGGCTTGC-3' | 4 |

Preparation of Recombinant α-1-Antichymotrypsin Having Met—Ala—Set N-Terminal Extension Stable monomers were expressed directly by eliminating the N-terminal cysteine residue through deletion of the nucleotides encoding the Leu—Cys—His—Pro (SEQ ID NO: 6) within the N-terminal sequence Met—Ala—Ser—Leu—Cys—His—Pro (SEQ ID NO: encoded within the nucleotide sequence of wild type and analogue α-1-antichymotrypsins to produce the nucleotide sequence encoding α-1-antichymotrypsin, wild type or analogue, with Met—Ala—Ser N-terminal extension. As such, the amino acids leucine, cysteine, histidine and proline at amino acid positions −4 to −1 of wild type or analogue α-1-antichymotrypsin may be deleted. The N-terminal extension becomes methionine-alanine-serine at amino acid positions −3 to −1. Such extension may be accomplished by PCR amplification, as set forth above, of the entire coding sequence with an N-terminal primer 5'-CCCCATATGGCTAGCAACAGCCCACTTG-3' (SEQ ID NO: 1). The C-terminal primer 5'-TTTCATATGGCTAGCGCTCTAGGCTTGC-3' (SEQ ID NO: 4) in which the underlined sequence GCTAGC serves as the insertion site may be used. The underlined CTA sequence creates a TAG termination codon in the sense strand of the vector. The sequence may be cloned into pZMs. The amplified full-length sequence may be digested with NheI and inserted into the expression vector pZMs, which is digested with Nhe I. *E. coli* may then be transformed with pZMs containing the gene with the altered N-terminal extension. As such, analogues of antichymotrypsin may be produced by altering amino acid positions −4 to −1, such that the amino acids leucine, cysteine, histidine and proline are deleted. Similarly, Met—Ala—Ser may be used to create an N terminal extension of 7 nucleotides. The methods and procedures set forth above for the production of Met—Ala—Ser extension may be followed for this N-terminal extension.

Cassette Vector Preparation of the Analogue of Human α-1-Antichymotrypsin Having Amino Acid Substitutions at Positions 356 through 361 and 349, 350, and 361

The nucleic acid sequence coding for human α-1-antichymotrypsin was obtained according to the method disclosed in U.S. Pat. No. 5,079,336, incorporated herein by reference. The analogue of human α-1-antichymotrypsin wherein the amino acids corresponding to Thr—Leu—Leu—Ser—Ala—Leu (SEQ ID NO: 7) at amino acid positions 356 through 361 of wild-type α-1-antichymotrypsin are substituted with Ile—Pro—Met—Ser—Ile—Pro (SEQ ID NO: 8) was prepared from the α-1-antichymotrypsin cassette analogue disclosed in U.S. Pat. No. 5,079,336.

The cassette protein was produced by site directed mutagenesis of the DNA sequence coding for α-1-antichymotrypsin was carried out using a commercially available kit (BioRad (Richmond, Calif.) M13 Mutagenesis Kit) according to the manufacturer's instructions and the synthetic DNA primers 5'-GTTGAAACGCGTAATGGTCCTT-3', (SEQ ID NO: 9), to construct a Mlu I restriction endonuclease site and 5'-ACTGCTGTGGTACCAGATGCTTC-3', (SEQ ID NO: 10), to create a Kpn I restriction endonuclease site. The synthetic primers were synthesized using standard techniques. The altered gene was excised from double-stranded M13 with EcoR1 and treated with Mung bean nuclease to form a blunt end. This product was then inserted into blunt ended pZM vector, yielding the recombinant denoted pACT-CAS.

The Kpn I and Mlu I restriction sites are unique to the DNA sequence. Site directed mutagenesis created the Kpn I restriction at positions corresponding to amino acids 349 and 350, as shown in FIG. 1, changing Ala—Ala to Gly—Thr and creating the Mlu I restriction site at positions corresponding to 368 and 369 changing Val—Arg to Thr—Arg. The region between the restriction sites, i.e. the cassette, contains the active site of α-1-antichymotrypsin and can be removed with Kpn I and Mlu I to insert a desired DNA sequence.

The cassette portion of the sequence was excised with Kpn I and Mlu I. A corresponding cassette, containing sequence ATTCCAATGTCTATTCCT, (SEQ ID NO: 11), which was prepared synthetically using conventional techniques, was ligated into the cassette portion site to provide bases coding for Ile—Pro—Met—Ser—Ile—Pro (SEQ ID NO: 8) at amino acids 356–361 of wild-type α-1-antichymotrypsin. The vector formed is denoted herein as pACT-P3-P3'PI.

The DNA sequence and the derived amino acid sequence of the insert from one of the positive lambda-gt11 cDNA clones contained the entire coding region of the mature human α-1-antichymotrypsin. The insert also included a 12 nucleotide extension of the 5'-end encoding four amino acids that appear in the precursor of the mature protein.

Expression of rACTP3P3'PI

*E. coli* N4830-1 was transformed with pACT-P3P3'PI by standard calcium chloride methods as described by Sambrook et al., *Molecular Cloning: A Laboratory Manual*, second edition, Cold Spring Harbor Laboratory Press, Cold Spring Harbor, N.Y. (1989).

Small scale growth conditions and extraction

Fresh overnight cultures of *E. coli* strain N4830-1 transformed with pACT-P3P3'PI were diluted to 1.5% in LB broth containing ampicillin (Na$^+$ salt, 0.1 mg/ml) and grown at 30° C. in a shaking incubator to an $A_{600nm}$ of 0.18, induced by raising the temperature to 42° C. and grown for an additional five to eight hours. The cells were centrifuged and disrupted in a French press. The α-1-antichymotrypsin protein purified from the transformed cells is denoted rACTP3P3'PI.

Purification and characterization of recombinant α-1-antichymotrypsin

Large-scale growth of *E. coli*

*E. coli* strain N4830-1 transformed with pACT-P3P3'PI were grown in LB media containing ampicillin (Na$^+$salt, 0.1 mg/ml) at 30° C. to an $A_{600nm}$ of 0.18 in a 15 L carboy fitted with an oxygen bubbler. The cells were induced by raising the temperature to 42° C. and grown for an additional six hours to a final $A_{600nm}$ of approximately 0.9–1.0.

Extraction and column chromatography

All purification steps were carried out at 4° C. In a typical preparation of rACTP3P3'PI, cell paste was dispersed in 10 mM potassium phosphate buffer, pH 6.9 (25 ml) and lysed by three passes through a French press at 10,000 psi and 4° C. Cell debris was removed by centrifugation at 30,000×g for 30 minutes at 4° C. The supernatant (25 ml) was loaded onto a column (4.9 cm$^2$×37 cm) of Sepharose Fast Q (Pharmacia) that had been equilibrated to 50 mM Tris-Cl, pH 7.5, containing 50 mM KCl. Protein eluted with a linear gradient of KCl in 50 mM Tris-Cl, pH 7.5 (50–500 mM in 2 L). Fractions (15 ml) were monitored for protein by $A_{280nm}$ and assayed for antichymotrypsin activity as described herein. rACTP3P3'PI eluted at approximately 200 mM KCl. Fractions containing rACTP3P3'PI were combined and dialyzed against two volumes (2.5 L each) of 10 mM potassium phosphate buffer, pH 6.9 over 48 hours. The dialyzed solution was then applied to a DNA-cellulose column (1.7 cm$^2$×20 cm) that had been pre-equilibrated with 10 mM potassium phosphate, pH 6.9, containing 10 mM KCl. After loading, the column was first washed with the same buffer (20 ml). The column was eluted with a linear gradient of KCl (10–500 mM, 300 ml) in the same buffer. Fractions (8 ml) were assayed for protein and antichymotrypsin activity as described herein. rACTP3P3'PI eluted at approximately 350 mM KCl. Fractions containing antichymotrypsin activity were analyzed for purity by SDS-PAGE, performed according to Laemmli, *Nature* (London) 1970, 227, 680. Each portion was concentrated by ultrafiltration using Amicon YM-10 membranes and dialyzed overnight against 50 mM Tris-Cl, pH 7.5 (500 ml). In some cases recombinant protein was further purified on an FPLC Mono Q anion exchange column, using the conditions described above.

Antichymotrypsin activity assays

Fractions (1.0 ml) were collected and assayed for antichymotrypsin activity which was measured as the inhibition of the chymotrypsin-catalyzed hydrolysis of substrate N-suc-Ala—Ala—Pro—Phe-p-nitroanilide (0.1 ml of a 10 mM solution in 90% DMSO), DelMar et al., Anal. Biochem. 1979, 99, 316. A typical chymotrypsin assay contained (in 1.0 ml): 100 mM Tris-Cl buffer, pH 8.3, 0.005% (v/v) Triton X-100, bovine pancreatic chymotrypsin (18 kmmol) and column eluate (0.005–0.5 ml). The assay mixture was pre-incubated at room temperature for 5 minutes, substrate (0.01 ml of a 10 mM solution in 90% DMSO) was added and remaining chymotrypsin activity was determined by the rate of change in $A_{410nm}$ caused by the release of p-nitroaniline. Measurements of optical absorbance were conducted at 25° C. using a spectrophotometer (Hewlett Packard 8452A) fitted with a temperature controlled sample compartment.

The amount of active rACTP3P3'PI present was determined by titration of a solution of chymotrypsin of known concentration and activity with varying amounts of partially purified rACTP3P3'PI fractions. The amount of active chymotrypsin present after incubation with the inhibitor-containing solutions was then determined using the chymotrypsin activity assay. Concentration of chymotrypsin was determined using the active-site titration method of Ardelt and Laskowski, *Biochemistry*, 1985, 24, 5313.

Inhibition of Human Neutrophil Elastase Materials and Methods

HNE and α1PI were obtained from CalBiochem. Substrates were obtained from Sigma Chemical Co. (St. Louis, Mo.). Standard proteins for SDS gels were from BioRad.

Determination of Inhibitor and Protease Concentrations rACTP3P3'PI and α1PI concentrations were determined by active site titration using bovine chymotrypsin. Chymotrypsin concentrations were standardized by titration with the active titrant, N-trans-cinnamoylimidazole according to the method of Schonbaum et al., *J. Biol. Chem.*, 1961, 236, 2930. HNE concentrations were determined by titration with standardized glPI. This value was used to determine a specific activity for HNE of 0.61 nmol product min m/nmol HNE measured under standard assay conditions as described by Nakajima et al., *J. Biol. Chem.*, 1979, 254, 4027 (0.1M HEPES pH 7.5, 0.5M NaCl, 9% $Me_2SO_4$, 1 mM N—MeO—Suc—Ala—Ala—Pro—Val—pNA). Para-nitroaniline formed was quantified using $e_{410}=8800\ M^{-1}cm^{-1}$.

Titrations and Time Course Studies

Titration reactions were performed in 0.50 ml containing 0.1M Tris-HCl, pH 8.0, 0.1M NaCl, 0.01% Triton X-100. HNE concentrations ranged between 150–400 Incubations were usually for thirty minutes at 25° C. Residual activity was measured by dilution of a sample aliquot in 1 ml standard buffer so that initial hydrolytic rates of controls were between 0.4 and 0.75 A absorbance units 410/min. Hydrolytic rates were continuously monitored for three minutes in either a Beckman DU of Gilford 260 spectrophotometer. Time course studies were performed similarly except that reaction volume was increased so that aliquot could be repeatedly removed from the same reaction mixture as time progressed.

Determination of Inactivation Rate Constants

Rate constants were determined under pseudo-first order conditions in the presence of substrate (0.5–1 mM) as described in Petersen and Clemmensen, *Biochem. J.*, 1981, 199, 121. Progress curves were monitored for ten to fifteen minutes and changes were measured at ten second intervals. Instantaneous velocity was determined by linear least square fitting of the absorbance measurements collected for every one minute interval. k', the apparent rate constant in the presence of substrate was determined by least square fitting of the data (plots of velocity vs. time), to an exponential $Ae^{-kt}$. The apparent rate constant was then corrected for substrate concentration according to the relationship, $k_{obs}=$ k'(Km/Km+S) where Km values measured were 0.40 mM in reactions containing 0.1M NaCl and 0.14 in reactions performed at 0.5 mM NaCl.

Ionic strength did not have significant effect on $k_{obs}$; values reported are the mean and standard deviation of measurements made at both ionic strengths.

SDS Gel Electrophoresis

Reactions were stopped after thirty minutes by the addition of PMSF (final concentration 0.5 mM) o After an incubation period of ten minutes, denaturing buffer including 2% SDS and 5 mM DTT (24) was added and samples were heated at 90° C. for ten minutes. Proteins were resolved on a 7.5% gel and visualized by staining with Coomassie Brilliant Blue.

Reaction of Recombinant Antichymotrypsin (rACT) with HNE

The interaction of HNE with recombinant human α-1-antichymotrypsin (rACT), prepared as disclosed in U.S. Pat. No. 5,079,336, showed no stable inhibition. At high inhibitor to elastase (I/E) ratios (25–30:1), initial rates of hydrolysis were lower than control and increased in a time and salt dependent manner to control levels of enzyme activity. SDS gel analysis of the reaction products taken as a function of time demonstrated the slow accumulation of cleaved fACT with no evidence of a stable complex. In control experiments, titration of HNE with α1PI was linear to a stoichiometry of inhibition (SI) of 1 and complexes formed at all I/E ratios were stable for at least twenty four hours in 0.15M NaCl, 0.1M Tris pH 8.0.

Reaction of rACTP3P3'PI With HNE and Antichymotrypsin

The time course of inhibition of HNE with rACTP3P3'PI showed an immediate loss in activity followed by a slow regeneration of free enzyme occurring in 0.1M NaCl over approximately twenty hours, indicating the formation of a very stable enzyme/inhibitor complex. By comparison, in 0.4M NaCl, this variant completely released HNE over the same period of time. The SI was independent of ionic strength and titrated to 1.4. The stability of the rACTP3P3'PI/HNE complex was demonstrated by the detection of high molecular weight reaction products on SDS-PAGE gel analysis. Under pseudo-first order conditions an apparent second order rate constant of $10^5 M^{-1}S^{-1}$ (n=6) was obtained for HNE and $1.8\times 10^4 M^{-1}s^{-1}$ for chymotrypsin compared to $3.0\times 10^5 M^{-1}S^{-1}$ for the rACTL358M/chymotrypsin interaction (rACT L358M is an α-1-antichymotrypsin analogue wherein the leucine at amino acid position 358 is substituted with methionine). The 1:1 titration of the rACTP3P3'PI with chymotrypsin indicated that the alterations at positions P10, P9 and P10' arising from the cassette vector did not change the SI value of the serpin with respect to this enzyme. While the rACTP3P3'PI had many of the properties of an efficient inhibitor of HNE, it did not attain the rate constant of α1PI with HNE($\sim 10^7 M^{-1} S^{-1}$) nor did the complex have the same degree of stability.

Various modifications of the invention in addition to those shown and described herein will be apparent to those skilled in the art from the foregoing description. Such modifications are also intended to fall within the scope of the appended claims.

What is claimed:

1. An analogue of human α-1-antichymotrypsin wherein the amino acid at position 358 is selected from the group consisting of isoleucine, valine, alanine, aspartic acid, threonine, and glutamic acid, said analogue having neutrophil elastase inhibiting activity.

2. An analogue of claim 1 wherein the amino acid at position 358 is isoleucine.

3. An analogue of claim 1 wherein the amino acid at position 358 is valine.

4. An analogue of claim 1 wherein the amino acid at position 358 is alanine.

5. An analogue of claim 1 wherein the amino acid at position 358 is aspartic acid.

6. An analogue of claim 1 wherein the amino acid at position 358 is threonine.

7. An analogue of claim 1 wherein the amino acid at position 358 is glutamic acid.

8. An analogue of human α-1-antichymotrypsin wherein the amino acids corresponding to Thr—Leu—Leu—Ser—Ala—Leu (SEQ ID NO: 7) at amino acid positions 356 through 361 of wild-type α-1-antichymotrypsin are substituted with Ile—Pro—Xxx—Ser—Ile—Pro (SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine; said analogue having neutrophil elastase inhibiting activity.

9. The analogue of human α-1-antichymotrypsin of claim 8 wherein the amino acids corresponding to Ala—Ala at amino acid positions 349 and 350 of wild-type α-1-antichymotrypsin are substituted with Gly—Thr and the amino acids corresponding to Val—Arg at amino acid positions 368 and 369 of wild-type α-1-antichymotrypsin are substituted with Thr—Arg.

10. An analogue of claim 1 optionally having a proline at at least one of the amino acid positions 356, 357, 359, 360 and 361.

11. The analogue of claim 1 wherein said human α-1-antichymotrypsin comprises the amino acid sequence set forth in FIG. 1 wherein amino acid position 358 is selected from the group consisting of isoleucine, valine, alanine, aspartic acid, threonine, and glutamic acid, said analogue optionally having a proline at at least one of the amino acid positions 356, 357, 359, 360 and 361.

12. A purified nucleic acid sequence coding for an analogue of human α-1-antichymotrypsin wherein the amino acid at position 358 is selected from the group consisting of isoleucine, valine, alanine, aspartic acid, threonine, and glutamic acid, said analogue optionally having a proline at at least one of the amino acid positions 356, 357, 359, 360, and 361.

13. A purified nucleic acid sequence coding for an analogue of human α-1-antichymotrypsin wherein the amino acids corresponding to Thr—Leu—Leu—Ser—Ala—Leu (SEQ ID NO: 7) at amino acid positions 356–361 are of wild-type α-1-antichymotrypsin are substituted with Ile—Pro—Xxx—Ser—Ile—Pro /SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine.

14. An expression vector comprising the nucleic acid sequence of claim 12.

15. An expression vector comprising the nucleic acid sequence of claim 13.

16. A host cell capable of expressing the nucleic acid sequence of claim 12.

17. A host cell capable of expressing the nucleic acid sequence of claim 13.

18. A cell culture capable of expressing analogue of human α-1-antichymotrypsin wherein the amino acid at position 358 is selected from the group consisting of isoleucine, valine, alanine, aspartic acid, threonine, and glutamic acid, said analogue optionally having a proline at at least one of the amino acid positions 356, 357, 359, 360 and 361.

19. A cell culture capable of expressing analogue of human α-1-antichymotrypsin wherein the amino acids corresponding to Thr—Leu—Leu—Ser—Ala—Leu (SEQ ID NO: 7) at amino acid positions 356 through 361 of wild-type α-1-antichymotrypsin are substituted with Ile—Pro—Xxx—Ser—Ile—Pro (SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine, obtained by transforming a cell line with an expression vector of claim 15.

20. A protein preparation comprising the analogue of human α-1-antichymotrypsin of claim 1.

21. A protein preparation comprising the analogue of human α-1-antichymotrypsin of claim 8.

22. A protein preparation comprising the analogue of human α-1-antichymotrypsin of claim 7.

23. A method of producing an analogue of human antichymotrypsin wherein the amino acids-corresponding to Thr—Leu—Leu—Ser—Ala—Leu (SEQ ID NO: 7) at amino acid positions 356 through 361 of wild-type α-1-antichymotrypsin are substituted with Ile—Pro—Xxx—Ser—Ile—Pro (SEQ ID NO: 8), wherein Xxx is selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine, comprising culturing a host cell capable of expressing said analogue of human α-1-antichymotrypsin to produce a mixture of cells and medium containing said analogue of human α-1-antichymotrypsin.

24. The method of claim 23 further comprising the step of purifying said mixture to produce said analogue of human α-1-antichymotrypsin in purified form.

25. The method of claim 23 wherein said analogue of human α-1-antichymotrypsin is encoded by the nucleic acid sequence of FIG. 1 having amino acid positions 356–361 substituted with Ile—Pro—Xxx—Ser—Ile—Pro (SEQ ID NO: 8), wherein Xxx is selected from the group consisting of methionine, tryptophan, alanine, asparagine, aspattic acia, cysteine, glutamine, glutamic acid, glycine, histidine, isoleucine, lysine, phenylalanine, proline, serine, threonine, tyrosine, and valine.

26. A composition comprising a pharmaceutically acceptable amount of an analogue of human α-1-antichymotrypsin wherein the amino acid corresponding to position 358 is selected from the group consisting of isoleucine, valine, alanine, aspartic acid, threonine, and glutamic acid; and a pharmaceutically acceptable carrier.

27. A composition comprising a pharmaceutically acceptable carrier amount of an analogue of human antichymotrypsin wherein the amino acids corresponding to Thr—Leu—Leu—Ser—Ala—Leu (SEQ ID NO: 7) at amino acid position 356 through 361 of wild-type α-1-antichymotrypsin are substituted with Ile—Pro—Xxx—Ser—Ile—Pro (SEQ ID NO: 8), wherein Xxx is selected from the group consisting of methionine, tryptophan, alanine, asparagine, aspattic acid, cysteine, glutamine, glutamic acid, glycine, histidine, isoleucine, lysine, phenylalanine, proline, serine, threonine, tyrosine, and valine.

28. The composition of claim 26 for treating inflammation of the lung.

29. The composition of claim 26 for treating inflammatory bowel disease.

30. The composition of claim 6 for treating skin inflammation.

31. The composition of claim 26 for treating pancreatitis.

32. The composition of claim 26 for treating glomerulonephritis.

33. The composition of claim 26 for preventing reperfusion injury.

34. The composition of claim 26 for treating sepsis.

* * * * *

UNITED STATES PATENT AND TRADEMARK OFFICE
CERTIFICATE OF CORRECTION

PATENT NO. : 5,674,708　　　　　　　　　　　　Page 1 of 4

DATED : Oct. 7, 1997

INVENTOR(S) :
　　Cooperman et al.

It is certified that error appears in the above-indentified patent and that said Letters Patent is hereby corrected as shown below:

At col 3, line 15, please insert --α-1--- before "antichymotrypsin".

At col 3, line 22, please insert --α-1--- before "antichymotrypsin".

At col 4, line 51, please insert --α-1--- before "antichymotrypsin".

At col 5, line 2, please insert --α-1--- before "antichymotrypsin".

At col 5, line 5, please insert --α-1--- before "proteinase".

At col 5, line 14, after "$M^{-1}$", please insert --$s^{-1}$--.

At col 5, line 15, after "homologous to", please insert --α---.

At col 6, line 12, please delete "Serfaria" and insert therefor --Serratia--.

At col 8, line 2, after "by" please insert a space before "elaborating".

At col 8, line 34, please delete "ile" and insert therefor --Ile--.

UNITED STATES PATENT AND TRADEMARK OFFICE
CERTIFICATE OF CORRECTION

PATENT NO. : 5,674,708

DATED : Oct. 7, 1997

INVENTOR(S) : Cooperman et al.

It is certified that error appears in the above-indentified patent and that said Letters Patent is hereby corrected as shown below:

At col 11, in Table 1, row 1, please underline GCTAGC.

At col 11, in Table 1, row 4, please underline GCTAGC.

At col 12, line 28, please insert --α-1--- before "antichymotrypsin".

At col 12, line 64, please underline GCTAGC and CTA.

At col 12, line 65, please underline GCTAGC.

At col 12, line 66, please underline CTA.

At col 13, line 6, please insert --α-1--- before "antichymotrypsin".

At col 15, line 40, please delete "g1P1" and insert therefor --α1P1--.

At col 15, line 41, please delete "min m" and insert therefor --min$^{-1}$--.

At col 15, line 51, after 150-400 please insert --nM.--

At col 15, line 56, after "0.75", please delete "A" and insert therefor --Δ--.

At col 16, line 36, please delete "fACT" and insert therefor --rACT--.

At col 21, line 22, please delete "aspattic" and insert therefor --aspartic--.

UNITED STATES PATENT AND TRADEMARK OFFICE
CERTIFICATE OF CORRECTION

PATENT NO. : 5,674,708

DATED : Oct. 7, 1997

INVENTOR(S) : Cooperman et al.

It is certified that error appears in the above-indentified patent and that said Letters Patent is hereby corrected as shown below:

At col 21, line 39, after "through", please insert a space before "361".

At col 21, line 42, please delete "aspattic" and insert therefor --aspartic--.

At col 22, line 27, after "Pro", please delete "/" and insert therefor --(--.

At col 22, line 43, please delete "aspattic" and insert therefor --aspartic--.

At col 22, line 54, please delete "aspattic" and insert therefor --aspartic--.

At col 22, line 64, after "claim", please delete "7" and insert therefor --9--.

At col 22, line 65, please insert --α-1-- before "antichymotrypsin".

At col 22, line 66, after "acids", please delete "-" and replace with a space before "corresponding".

At col 23, line 20, please delete "aspattic" and insert therefor --aspartic--.

At col 24, line 4, please insert --α-1-- before "antichymotrypsin".

UNITED STATES PATENT AND TRADEMARK OFFICE
CERTIFICATE OF CORRECTION

PATENT NO. : 5,674,708
DATED : Oct. 7, 1997
INVENTOR(S) : Cooperman, et al

It is certified that error appears in the above-identified patent and that said Letters Patent is hereby corrected as shown below:

At col 24, line 18, after "clain", please delete "6" and insert therefor --26--.

Signed and Sealed this

Third Day of March, 1998

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,674,708
DATED : Oct. 7, 1997
INVENTOR(S) : Cooperman et al.

It is certified that error appears in the above-indentified patent and that said Letters Patent is hereby corrected as shown below:

Title Page:

Please insert "*" next to the Date of Patent.

Please insert a Notice that the term of this patent shall not exceed beyond the expiration date of Pat. No. 5,612,194.

Signed and Sealed this

First Day of September, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 1:

```
CCCCATATGG CTAGCAACAG CCCACTTG                28
```

( 2 ) INFORMATION FOR SEQ ID NO: 2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

```
CCACAGGAAT AGACATTGGA ATGATTTTGA CTGCTGTGG    39
```

( 2 ) INFORMATION FOR SEQ ID NO: 3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 3:

```
CATTCCAATG TCTATTCCTG TGGAGACAAG GACCAT       36
```

( 2 ) INFORMATION FOR SEQ ID NO: 4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

```
TTTCATATGG CTAGCGCTCT AGGCTTGC                28
```

( 2 ) INFORMATION FOR SEQ ID NO: 5:

( i ) SEQUENCE CHARACTERISTICS:
        ( A ) LENGTH: 7 amino acids
        ( B ) TYPE: amino acid
        ( C ) TOPOLOGY: linear (ii) MOLECULE TYPE: protein (xi) SEQUENCE DESCRIPTION: SEQ ID NO: 5:

Met Ala Ser Leu Cys His Pro
     1          5

(2) INFORMATION FOR SEQ ID NO: 6:

(i) SEQUENCE CHARACTERISTICS:
    (A) LENGTH: 4 amino acids
    (B) TYPE: amino acid
    (C) TOPOLOGY: linear (ii) MOLECULE TYPE: protein (xi) SEQUENCE DESCRIPTION: SEQ ID NO: 6:

Leu Cys His Pro
     1

(2) INFORMATION FOR SEQ ID NO: 7:

(i) SEQUENCE CHARACTERISTICS:
    (A) LENGTH: 6 amino acids
    (B) TYPE: amino acid
    (C) TOPOLOGY: linear (ii) MOLECULE TYPE: protein (xi) SEQUENCE DESCRIPTION: SEQ ID NO: 7:

Thr Leu Leu Ser Ala Leu
     1          5

(2) INFORMATION FOR SEQ ID NO: 8:

(i) SEQUENCE CHARACTERISTICS:
    (A) LENGTH: 6 amino acids
    (B) TYPE: amino acid
    (C) TOPOLOGY: linear (ii) MOLECULE TYPE: protein (xi) SEQUENCE DESCRIPTION: SEQ ID NO: 8:

Ile Pro Xaa Ser Ile Pro
     1          5

(2) INFORMATION FOR SEQ ID NO: 9:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 9:

GTTGAAACGC GTAATGGTCC TT         22

(2) INFORMATION FOR SEQ ID NO: 10:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 10:

```
              ACTGCTGTGG TACCAGATGC TTC                           23
```

( 2 ) INFORMATION FOR SEQ ID NO: 11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 11:

```
              ATTCCAATGT CTATTCCT                                 18
```